United States Patent [19]

Fick

[11] Patent Number: 4,743,402

[45] Date of Patent: May 10, 1988

[54] NOVEL SUNFLOWER PRODUCTS AND METHODS FOR THEIR PRODUCTION

[75] Inventor: Gerhardt N. Fick, Breckenridge, Minn.

[73] Assignee: SIGCO Research Inc., Breckenridge, Minn.

[21] Appl. No.: 769,502

[22] Filed: Aug. 26, 1985

Related U.S. Application Data

[62] Division of Ser. No. 672,359, Nov. 16, 1984, Pat. No. 4,627,192.

[51] Int. Cl.$^4$ .............................................. C11B 1/10
[52] U.S. Cl. .................. 260/412.2; 420/601
[58] Field of Search .................. 426/601; 260/412.2

[56] References Cited

PUBLICATIONS

Knowles, P. F., *Crop Science*, vol 4: 406–409, (1964).
Knowles P. F., *Journal of the American Oil Chemists' Society*, vols. 46, 49, Nos. 1, 3, pp. 27–29, 130–132, (1972).
Knowles, P. F., *Economic Botany*, vol. 19, No. 1, (1965), pp. 53–62.
Karchenko, L. N., *Fiziologiya Rastenil*, 26: 1221–32, (1979).
Stumpf, P. K., *Fatty Acid Metabolism and Its Regulation*, (1984) pp. 155–179.
Knowles et al. *Economic Botany*, 19(1): 53–62 (1965).
Knowles P. F., *Economic Botany*, 37(4): 423–433 (1983).
Knowles P. F., *Improvement of Oil—Seed and Industrial Crops By Induced Mutations*, pp. 90–101.
Soldatov, K. I., *Proc. 7th Int'l Sunflower Conf.*, (1976), pp. 352–357.
Urie, A. L., *Crop Science*, vol. 25, (1985), pp. 986–989.
Miller et al., *Proc. Sunflower Research Workshop 10* (Minot. DN; Jan. 26, 1983)—abstract.
Fick, *Proc. Sunflower Research Workshop 9*, (Bismarck, N. Dak.; 1984).
Miller et al., *North Dakota Farm Research* (vol. 42, No. 2), 1984 (Sep.–Oct.) issue; pp. 27 & 32.
Bailey's Ind. Oil and Fat Products, vol. 1, (4th Ed. 1979), pp. 384 and 370.
Journal: Food and Nutrition, No. 7–8, "The Relative Amounts of Fatty Acids in Sunflower Oil of Certain Inbred Lines and NS Hybrids of Sunflowers", T. Cuprina, I. Veresbaranji, Institute for Agriculture, University of Novi Sad, Yugoslavia (with English translation).
Chemical Abstract 92: 20808x–"Refining of Sunflower Oil with High Oleic Acid Content", Zalevskaya, L. M. et al., (1979).
Chemical Abstracts 92: 4880j–"Chemical Composition of Sunflower Seeds Taken From Various Parts of the Flowerhead", Ivanov, P. et al., (1978).
"Lipids in the Seeds of a New High-Oleic Acid Variety of Sunflower", L. N. Kharchenko et al., Russian w/English translation attached.
Chemical Abstracts 107:57649a, "Comparative Characteristics of Lipids of High Olein Sunflower:, A. K. Mosyan et al., 1987.
Chemical Abstracts, 90:4692h, "Glyceride Composition of Sunflower Seed Oil with Different Linoleic and Oleic Acid Contents, Kharchenko, 1978.

*Primary Examiner*—Charles F. Warren
*Assistant Examiner*—Elizabeth A. Hanley
*Attorney, Agent, or Firm*—Foley & Lardner, Schwartz, Jeffery, Schwaab, Mack, Blumenthal & Evans

[57] ABSTRACT

A sunflower seed is disclosed which has both a high oleic acid content and a low linoleic acid content. Also disclosed is a sunflower seed which has a white or gray seed coat and which contains approximately 80% or greater by weight of oleic acid. Also described are novel sunflowers for producing the disclosed seed and an oil product derived from the seed.

13 Claims, 2 Drawing Sheets

NOVEL SUNFLOWER PRODUCTS AND METHODS FOR THEIR PRODUCTION

This is a division, of application Ser. No. 672,359, filed Nov. 16, 1984, now U.S. Pat. No. 4,627,192.

BACKGROUND OF THE INVENTION

This invention relates to a novel sunflower hybrid, to products obtained from the novel hybrid, and to methods for producing the sunflower products.

The sunflower (genus Helianthus) is second only to the soybean as a source worldwide for vegetable oil. In the United States there are approximately four million acres planted annually in sunflower, primarily in the Dakotas and in Minnesota. Average sunflower yields in the United States range from about 1200 to about 1400 kg/hectacre, with the oil content from harvested seed averaging about 44% on a dry weight basis Increasing both yield and oil content are currently major objectives in sunflower breeding programs in the United States, Canada, the USSR, and elsewhere; other objectives of such programs include earlier plant maturity, shorter plant height, uniformity of plant type, and disease and insect resistance The very rapid expansion over the last decade of acreage planted in sunflower in the United States is due in part to several important developments in the field of sunflower breeding and varietal improvement. One significant development was the discovery of cytoplasmic male sterility and genes for fertility restoration, a discovery that allowed for the production of hybrid sunflower. The hybrids thus produced were introduced during the early 1970's. They showed about a 25% yield advantage over the open-pollinated varieties, improved disease resistance, greater uniformity in height and flowering; and a greater degree of self-compatibility, which alleviates the dependency on high insect pollinator populations for good seed set.

A description of cytoplasmic male sterility (CMS) and genetic fertility restoration in sunflowers is presented by Fick, "Breeding and Genetics," in SUNFLOWER SCIENCE AND TECHNOLOGY 279-338 (J. F. Carter ed. 1978), the contents of which are incorporated herein by reference. The production of a particular sunflower hybrid using CMS is described in U.S. Pat. No. 4,378,655, the contents of which are also incorporated herein by reference. Although cytoplasmic male sterility is now the technique of choice for producing sunflower plants with substantially nonfunctional pollen for subsequent use in producing hybrids, other methods, also described in the aforementioned U.S. patent, are available. These include the use of complete or partial genetic sterility based on the presence of recessive genes and the application of chemical gametocides. Plants having a high level of self-incompatibility can also be used in a method for hybrid production.

Another important development in sunflower breeding was the introduction into the United States of high oil varieties from the USSR in the mid-1960s. These varieties had oil percentages (total oil relative to seed weight) in the range of 40-45% as compared to 30-35% for varieties grown previously. The oleic acid percentage for the oil of these and other commercially grown varieties varied, especially with environment, but rarely exceeded 40 percent. In the late 1970's researchers in the USSR reported in the the production by chemical mutagenesis of an open-pollinated sunflower cultivar ("Pervenets") which produced an oil having an oleic acid content, expressed as percentage of total fatty acid content, of approximately 70% to 80%, with proportionately less linoleic acid. See Soldatov, "Chemical Mutagenesis in Sunflower Breeding," in PROC. 7th INT'L SUNFLOWER CONF. (Krasnodar, USSR 1976) 352-57. Pervenets germplasm became generally available to sunflower breeders in the United States after 1980.

Sunflower oil is comprised primarily of palmitic, stearic, oleic, and linoleic acids, with oleic and linoleic accounting for about 90% of the total fatty acid content in conventional oils. It has been recognized that there was an inverse relationship between oleic and linoleic acid which was highly influenced by environment, especially temperature during the growing season. Heretofore, cool northern climates yielded high linoleic acid-content sunflower seed, whereas high oleic acid values were characteristic of seed grown in warmer southern areas. While a high linoleic acid concentration is desirable in sunflower oils used in soft margarines and salad dressings, a high oleic acid content is preferred for many other applications, since oleic acid is oxidatively more stable than linoleic acid. As a consequence, oxidative stability of conventional crude sunflower oil derived from seed grown in southern climates is nearly twice that of crude oil extracted from northern-grown seed.

With the Pervenets cultivar, however, an increase in oleic acid percentage of total fatty acid content from 64% to 79% during seed formation and ripening was observed in conjunction with a decrease in linoleic acid of from 26% to 15%, see Soldatov, supra, compared to a 21-54% increase in the linoleic acid content of conventional seed. Moreover, while higher growing temperatures promoted rapid oleic acid development in Pervenets plants, the comparatively higher oleic acid-linoleic acid content ratio characteristic of the cultivar remained substantially unaffected by environmental conditions. See Kharchenko, "Genotypic and Phenotypic Mechanisms Ensuring Regulation of Fatty Acid Biosynthesis in Sunflower Seeds," *Fiziologiya Rastenii* (Russian) 26:1226-32 (1979).

The development of the Pervenets cultivar therefore held particular significance for the possible enhancement of oxidative stability in sunflower oils. As an open-pollinated cultivar, however, Pervenets is heterogeneous for high oleic acid content; that is, individual plants producing various levels of oleic acid are present in the variety and the high oleic trait is not expressed reproducibly over many generations of sunflower plantings. Even for those Pervenets sunflower plants which do produce high oleic seed, the content of linoleic acid, expressed as percentage of the total amount of fatty acids, can be substantial, ranging as high as 26% or more. See Soldatov, supra at page 356 . Moreover, the Pervenets cultivar does not consistently express various other characteristics, such as adequate disease resistance, which may be critical to the commercial viability of a new crop. Pervenets seed is also basically indistinguishable from the black or black-and-gray striped seed produced by conventional, commercially grown oilseed sunflower hybrids. As a consequence, Pervenets seed cannot be readily recognized as such, if it is mixed with other oilseed at some point during the multi-stage processing of seed into oil.

SUMMARY OF THE INVENTION

It is therefore an object of the present invention to provide a sunflower seed combining a high oleic acid content with a low linoleic acid content.

It is also an object of the present invention to provide a sunflower seed which consistently yields a high oleic acid oil and which is easily distinguished, on the basis of seed coat coloring, from other sunflower seeds.

It is another object of the present invention to provide a new sunflower which is true-breeding, under a wide variety of growing conditions, for the trait of high oleic acid content.

It is a further object of the present invention to provide new sunflower plants that can be used efficiently to produce parent lines and hybrids possessing desirable agronomic traits.

It is yet another object of the present invention to provide a method for producing a hybrid sunflower that has seed which is high in oleic acid.

It is still another object of the present invention to provide a novel sunflower oil possessing a markedly enhanced shelf life.

In accomplishing the foregoing objects, there has been provided, in accordance with the present invention, a sunflower seed having an oleic acid content greater than about 80% relative to the total fatty acid content of the seed, and a ratio of the amount of linoleic acid in the seed to the amount of oleic acid in the seed of less than approximately 0.09. In a preferred embodiment, the aforementioned ratio is between about 0.01 and about a 0.09.

There has also been provided in accordance with the present invention a sunflower seed which has an oleic acid content of approximately 80% or greater, relative to the total fatty acid content of the seed, and which is either white or gray in color. In one preferred embodiment, the sunflower seed of the present invention is produced by a process comprising the step of crossing a first parent which comprises Pervenets germplasm encoding high oleic acid content with a second parent which comprises a genetic determinant for white seed color. In another preferred embodiment, the sunflower seed of the present invention is produced by a process comprising the step of crossing a first parent which yields white seed with a second parent which yields black seed, at least one of the parents containing Pervenets germplasm coding for high oleic acid content.

In accordance with another aspect of the present invention, there has been provided a hybrid sunflower which is cytoplasmic male sterile or, alternatively, which comprises a genetic determinant encoding fertility restoration, and which, in addition, produces either white or gray seed having an oleic acid content of greater than 80%, relative to the total fatty acid content of the seed.

In accordance with yet another aspect of the present invention, there has been provided a sunflower oil containing approximately 80% or greater of oleic acid, relative to the total fatty acid content of the oil, which oil has a ratio of linoleic acid content to oleic acid content of less than approximately 0.09.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

Figure 1:
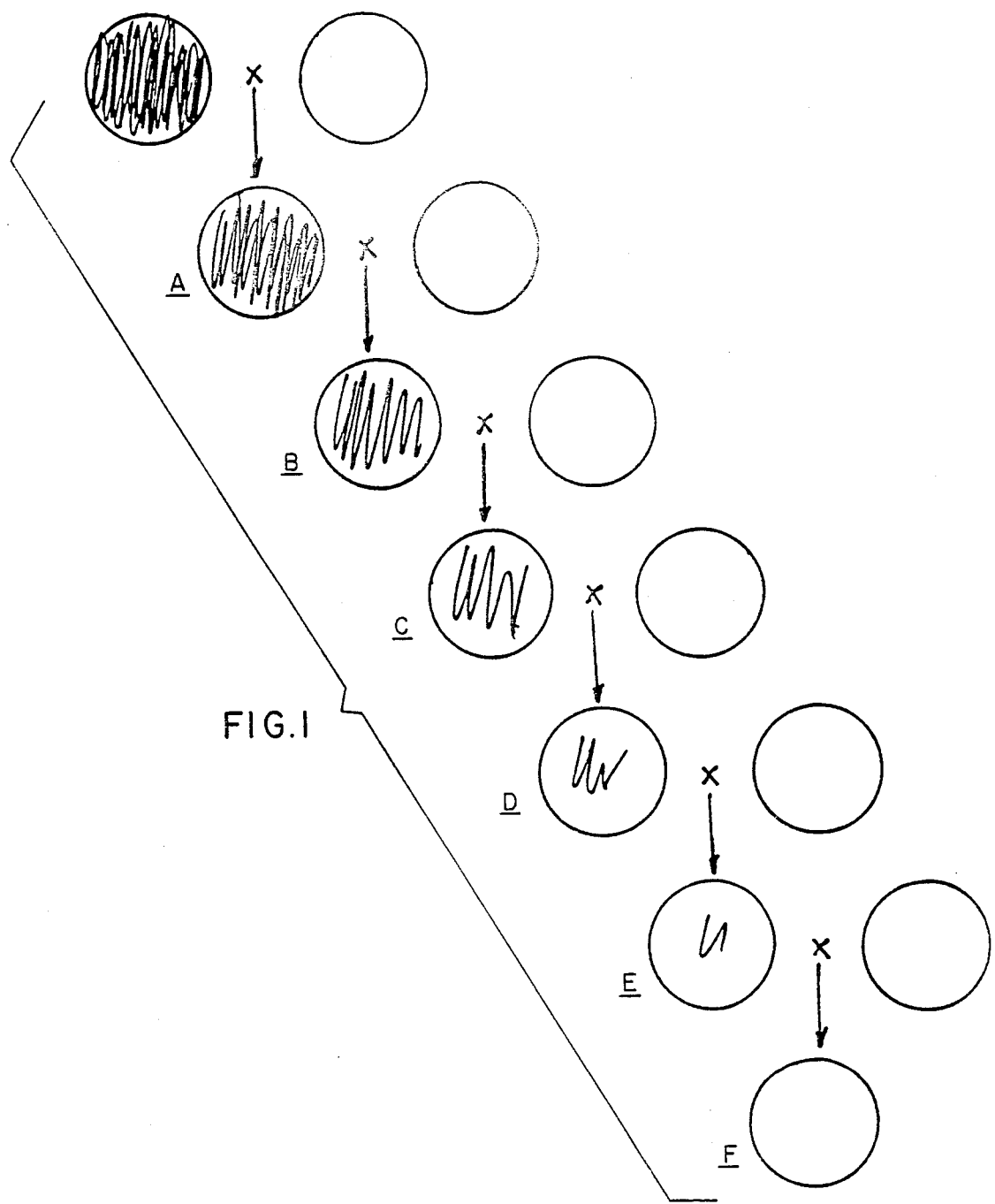
FIG. 1 schematically depicts a method for developing and maintaining a CMS line within the present invention.

For the purposes of the present description, the terms "cultivar" and "variety" are used synonymously to refer to a group of plants (e.g., Pervenets) within a species (*Helianthus annuus*) which share certain constant characters that separate them from the typical form and from other possible varieties within that species. While possessing at least one distinctive trait, a variety like Pervenets is also characterized by a substantial amount of overall variation between individuals within the variety, based primarily on the Mendelian segregation of traits among the progeny of succeeding generations. A "line," as distinguished from a "variety," denotes a group of plants which display less variation between individuals, generally (although not exclusively) by virtue of several generations of self-pollination. In addition, a "line" is defined, for the purpose of the present invention, sufficiently broadly to include a group of plants vegetatively propagated from a single parent plant, using tissue culture techniques. The use of such lines to develop new hybrids is described in U.S. Pat. Nos. 4,326,358 and 4,381,624, the contents of which are incorporated herein by reference. A variety or a line is considered "true-breeding" for a particular trait if it is genetically homozygous for that trait to the extent that, when the true-breeding variety or line is self-pollinated, a significant amount of independent segregation of the trait among the progeny is not observed.

As noted above, the content of various fatty acids, such as oleic and linoleic, which is characteristic of oil from a given seed sample is commonly expressed as a percentage of the total fatty acid fraction in the oil. This convention will be followed in the following description, unless otherwise indicated. Dimensionless ratios of linoleic acid content to oleic acid content, which are also mentioned below, are calculated by dividing the linoleic acid percentage of total fatty acids by the like percentage of oleic acid.

The novel sunflower of the present invention reproducibly expresses the high oleic trait of the Pervenets cultivar against a phenotypic background of disease-resistance, high seed yield, and other agronomic characteristics which is sufficiently consistent for commercial applications. In contrast, the original cultivar displayed extensive variability in the expression of such characteristics. There was also a large amount of variability observed within the cultivar as to oleic acid content. Seed obtained from Pervenets selections grown in Minnesota averaged 71% oleic acid content, as determined by gas chromatographic analysis of oil obtained therefrom, but individual plants were characterized by significantly lower values. In contrast, sunflower seed of the present invention average in excess of 80% oleic acid content, and values as high as 94% have been obtained.

To produce the novel sunflower of the present invention, Pervenets-derived parent lines and varieties possessing the highest possible oleic acid content may be used to advantage, although any Pervenets germplasm can be used as starting material. Initial studies indicate that high oleic acid content is controlled by a single, partially dominant gene, although other genes affecting oleic acid content may be present in Pervenets germplasm. See Fick, "Inheritance of High Oleic Acid in Seed Oil of Sunflower," in PROC. SUNFLOWER RESEARCHERS WORKSHOP 9 (Bismarck, ND 1984), the contents of which are incorporated herein by reference. In any case, a preferred line can be obtained, following conventional sunflower breeding by self-pollination for a number of generations, usually three or more, of Pervenets progeny or of crosses of pervenets with other lines or varieties, selected for high oleic content.

After inbreeding has progressed to the point where progeny are true-breeding for oleic acid content, the Pervenets derived starting material is preferably converted to cytoplasmic male sterility (CMS), in accordance with the present invention, by crossing the selected Pervenets germplasm with a sunflower line, such as CMS HA89 (U.S. Department of Agriculture), that incorporates a cytoplasmic determinant for male sterity. The source of CMS HA89 and most other currently available CMS lines is from the material of Leclercq, "Cytoplasmic Sterility in the Sunflower," *Ann. Amelior. Plant.* (French) 19: 99–106 (1969).

Other sources for CMS determinants may be used in accordance with the present invention, including the open-pollinated composites of Whelan and Dedio, "Registration of Sunflower Germplasm Composite crosses CMG-1, CMG-2, and CMG-3" *Crop Sci.* 2: 832 (1980), and the CMS lines of Heiser, Jr., "Registration of Indiana-1 CMS Sunflower Germplasm," *Crop Sci.* 22: 1089 (1982). If the Pervenets line to be used has not been tested previously for combining ability, crosses with a cytoplasmic male sterile tester and subsequent evaluation of the sterile $F_1$ hybrid can provide valuable information on combining ability, as outlined by Fick, "Breeding and Genetics," supra at 293.

Progeny incorporating the CMS determinant, but otherwise increasingly less of the the genetic content of the original CMS parent, are obtained by recurrent backcrosses to the line derived from the Pervenets starting material, as shown in FIG. 1. From the first-generation progeny A, wherein 50% of the recurrent parent's genotype is statistically represented, through successive backcross generations B-F, the contribution of the recurrent parent increases, i.e., the genetic contribution of the nonrecurrent, male-sterile parent is reduced by half for each generation of backcrossing (in theory, B : 75% recurrent parent; C : 87.5%; D : 93.75%; E : 96.88%; F : 98.45%). The final progeny are virtually identical with the recurrent, high-oleic parent except that they are male sterile instead of fully fertile.

A high-oleic CMS line produced in accordance with the present invention does not produce viable pollen, but can be maintained and increased in conjunction with the original Pervenets-derived sunflower line that was used as the recurrent parent in the backcross conversion to CMS (the "maintainer (B) line") shown in FIG. 1. More specifically, the maintainer of the high-oleic CMS line is used to produce the female parent for a cross with a male parent that is homozygous for the genetic determinant encoding fertility restoration of the male sterile cytoplasm ("the restorer (R) line"), whereby fertile, pollen-producing hybrids result. Alternatively, another of the above-mentioned techniques, such as use of genetic sterility and chemical gametocides, can be applied to permit a parent incorporating Pervenets germplasm which encodes high oleic content to be used to produce sunflower hybrids in accordance with the present invention.

A suitable restorer line can be produced, in accordance with the present invention, by crossing Pervenets germplasm with any of the commonly available restorer lines, such as RHA274 (U.S. Department of Agriculture) or other lines possessing genes for restoration of male fertility. Lines and varieties thus derived which produce seed having 80% or higher oleic acid content, and which are true-breeding for at least the fertility restorer gene(s), can then be isolated by continuous self-pollination and crossed with the high-oleic CMS line previously described. By way of illustration, a high-oleic CMS line, designated "SIGCO 41A," was used, following the present invention, with a restorer line, designated "SIGCO 853R," developed out of a (Pervenets x RHA 274) cross to produce $F_1$ hybrid seed for commercial plantings yielding oil in excess of 80% oleic acid. The parent lines of the aforementioned cross share with other high oleic lines within the present invention various general characteristics, including:

1. light green to dark green stem and leaf color, with or without the presence of anthocyanin pigment,
2. light yellow, yellow, orange, and/or red flower color,
3. period to flowering of ranging from 45 to 90 days,
4. plant height between about 30 and about 180 cm, and
5. an oil percentage for seed of between about 35% and about 60% relative to total seed weight. (Certain specific characteristics of the respective parent lines are enumerated in Table 1.) The $F_1$ progeny of the (SIGCO 41A x SIGCO 853R) cross are single-flowered and grow to a height between about 90 and about 240 cm; otherwise, like other high oleic hybrids of the present invention, they display the same general characteristics listed above for the parent lines.

TABLE 1

Specific Characteristics of Parent Lines Used in (41A × 853R) Cross

| | SIGCO 41A | SIGCO 853R |
|---|---|---|
| Plant Height | 150–200 cm | 120 cm (approx.) |
| Flower Color | Medium Yellow | Medium Yellow |
| Flower Number | Single | Single* |
| Days to Flower (after planting) | approx. 70 | 65–72 |
| Stem/Leaf Color | Dark Green | Dark Green |
| Seed Color | Black with Gray Stripe | Black with Gray Stripe |
| Seed Oil Content | 2–3% less than USDA HA89 | 1–2% less than USDA RHA274 |
| Other | — | Relatively weak upper stem, with head horizontal to ground at maturity |

*In less than 5% of SIGCO 853R plants, branched heads arise from the leaf axils of the main stems.

Although sterility techniques, including the use of CMS determinants, may be advantageously applied in producing Pervenets-derived parent lines and varieties as well as hybrids within the present invention, the application of such techniques is not a prerequisite of the present invention. Parent lines and varieties meeting the requirements of the present invention, as set out in greater detail elsewhere herein, can be produced by manipulation of existing sunflower materials, using other conventional methods, based on successive selections and inbreeding, or newly developed molecular approaches to altering the genetic content of plants. See, e.g., Murai et al., "Phaseolin gene from bean is expressed after transfer to sunflower via tumor-inducing plasmid vectors," Science 222:476-82 (1983). In any event, the production of suitable parent lines and varieties in accordance with the present invention entails the elimination of a certain amount of variability, at least to the extent that an appreciable number of progeny derived from self-pollinating at least one of the parents produce seed having a high oleic acid content.

The oil derived from sunflower seed of the present invention is of unique character, particularly with regard to the stability over time of the oil of the present invention. For example, two samples of sunflower seed (designated in Table 2 as "M," for Minnesota-grown seed, and "T," for Texas-grown seed, respectively) obtained from sunflower plants of a parent line (SIGCO 41B) produced in accordance with the present invention were each ground in like sized lots, and the moisture level of the resulting compositions was adjusted to between 8% and 10%. For comparison purposes, a composite sample of seed from a number of open-pollinated sunflower plants representing selections from Pervenets was similarly processed.

TABLE 2

Composition and AOM Values of Sunflower and Safflower Oils

| | % of Total Fatty Acids (rounded off to nearest whole percent) | | | | |
|---|---|---|---|---|---|
| | Palmitic | Stearic | Oleic | Linoleic | AOM (Hours) |
| Safflower, normal[1] | 7 | 2 | 12 | 79 | 10 |
| Safflower, high-oleic[1] | 5 | trace | 80 | 15 | 35 |
| Sunflower, Northern[2] | 7 | 5 | 18 | 69 | 11 |
| Sunflower, Northern II[3] | 6 | 5 | 26 | 62 | 11 |
| Sunflower, Southern[3] | 5 | 4 | 51 | 38 | 18 |
| Sunflower, open-pollinated Pervenets selection (Minnesota) | 3 | 5 | 79 | 12 | 38 |
| Sunflower, high-oleic M (SIGCO 41B-Minnesota) | 3 | 5 | 87 | 4 | 60 |
| Sunflower, high-oleic T (SIGCO 41B-Texas) | 4 | 3 | 92 | 1.5 | 100 |

[1]Data from Purdy & Campbell, Food Technology 21:31A (1967).
[2]1983 typical commercial production (National Sunflower Assn.).
[3]Data from Morrison, J. Am. Oil Chemists Soc. 52:522 (1975).

Thereafter, each ground-seed composition was cooked in a sealed vessel for one hour at 130° C. Extraction was then performed in a Butt-type extractor, using commercial grade hexane as solvent, for four hours. The cooled compositions were reground and returned to the extractor for an additional four hours of extraction. The solvent was removed from the miscella, first by distillation to a pot temperature of 75° C. and finally in a roto-vac apparatus under reduced pressure over hot water to less than 10 mm mercury pressure.

The resulting crude extracted oils were each treated with sufficient 16° BE' (Baume) sodium hydroxide solution to neutralize the free fatty acid plus 1.8% excess (based on total oil weight) for 5 minutes at 65° C. under moderate agitation. The heavy soap phase was separated by centrifugation. Residual soap and impurities removal was accomplished by washing with approximately 15% by volume of water for 5 minutes at 90° C. followed by bleaching the clear oil obtained by centrifugation with 1% acid activated earth at 10 to 20 mm mercury pressure and 95° C. for 10 minutes. The activated earth was separated by suction filtration.

Approximately 300 grams of bleached oil for each sample were treated in an all-glass deodorizer with 5% steam at 250° C. under 4 mm mercury pressure for 1.5 hours. All three deodorized oils exhibited colors lighter than 10 yellow/1 red lovibond, free fatty acids less than 0.05%, zero peroxide values, and bland flavors with no trace of odor. Anisidine values were less than 0.5, indicating that a minimum of oxidation occurred during processing.

Fatty acid distributions were then determined by a standard procedure designated "CE 1-62" in OFFICIAL AND TENTATIVE METHODS, Volume 2 (1980), American Oil Chemists Society (AOCS), 508 South 6th Street, Champagne, IL 61820, modified to the extent that a 10-foot×⅛-inch stainless steel column packed with 11.4% 3-cyano propyl silicone on chromosorb W-AW 100/120 mesh was used. Active Oxygen Method (AOM) determinations were conducted according to AOCS procedure "CD 12-57." The AOM values and fatty acid profiles for the oil obtained from the SIGCO 41B samples M and T, and from the open-pollinated Pervenets selections, are shown in Table 2 along with the AOM values and fatty acid profiles for two safflower oils, two sunflower oils from seed grown in a northern climate, and one oil from a southern grown, conventional sunflower seed. Illustrative fatty acid content data derived by gas chromatographic analysis of seed oil from sunflower plants within the present invention are enumerated in Table 3.

Figure 2:
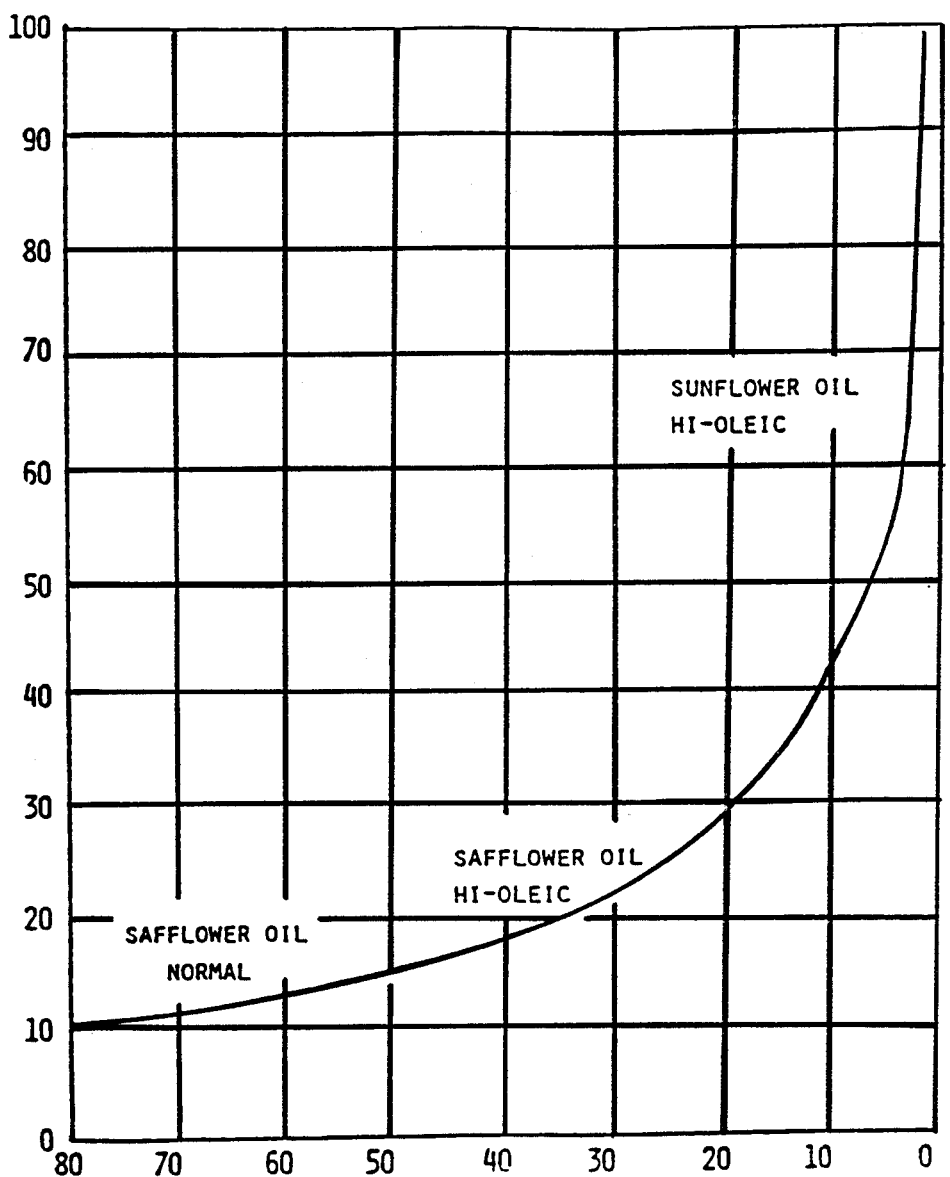
FIG. 2 presents a graph in which the stability of sunflower oil over time is plotted as a function of linoleic acid concentration.

As can be appreciated from the data in Table 2 the oil produced from the seed of the present invention displays an oxidative stability which is substantially enhanced over the stability of conventional safflower oils, conventional sunflower oils from seed grown in both northern and southern climates, and oil from a composite of open-pollinated Pervenets selections. The observed enhancement in AOM values for oil produced from seed of the present invention is attributed not only to increased oleic acid content but also to a low linoleic acid-to-oleic acid (L/O) ratio. The relationship between linoleic acid concentration and AOM value is shown in FIG. 2.

TABLE 3

Qualitative Analysis of Sunflower Oils of the Present Invention

| Plant From Which Seed was Obtained | % of Total Fatty Acids (rounded off to nearest whole percent) | | | |
|---|---|---|---|---|
| | Palmitic | Stearic | Oleic | Linoleic |
| A | 3 | 3 | 90 | 2 |
| B | 4 | 5 | 88 | 2 |
| C | 3 | 4 | 88 | 3 |
| D | 3 | 7 | 82 | 5 |
| E | 4 | 4 | 84 | 7 |
| F | 4 | 3 | 90 | 2 |
| G | 5 | 10 | 80 | 4 |
| H | 4 | 10 | 78 | 7 |
| I | 4 | 10 | 81 | 4 |
| J | | | | |

Even compared to seed obtained from the Pervenets cultivar, the L/O ratios for seed produced in accordance with the present invention are surprisingly low, as is also apparent from the data contained in Table 4.

The dramatic lowering of linoleic acid content, coupled with an oleic acid content of approximately 80% or greater by weight (see Table 3) is a key factor in the substantial improvement in shelf life for oils obtained from sunflower seeds within the present invention. In addition, as the comparison between samples M and T in Table 2 shows, the sunflower plants of the present invention do not display a high sensitivity to temperature or other environmental factors in their expression of the high oleic trait. Studies have shown that oleic acid content varied only 4 to 5 percentage units among plants of the present invention cultivated in widely different climates of Minnesota, Texas, Argentina, and Chile.

As another aspect of the present invention, high-oleic sunflower seed is produced which is characterized by highly distinctive seed coat coloring. As previously indicated, the seed of all oilseed hybrids which are grown commercially have coats which are black or black with fine gray stripes. Generally, the color of sunflower seeds is determined by the presence or absence of pigment in each of three different seed coat layers. Each layer may develop pigment independently of the other layers. The outer layer or epidermis may be free of pigment, fully pigmented dark brown or black, or possess striped patterns of dark brown or black. The second or corky layer may either lack pigment or contain anthocyanin so intense as to mask the pigments in the other layers. The third or innermost layer, often referred to as the armor layer, is either non-pigmented or black.

TABLE 4

Linoleic-to-Oleic Acid Ratios of Sunflower Oils

| Source | Ratio |
| --- | --- |
| Sunflower, Northern (See Table 2) | 3.8 |
| Sunflower, Northern II (See Table 2) | 2.3 |
| Sunflower, Southern (See Table 2) | 0.74 |
| Pervenets[1] | Approx. 0.11–0.18 (normal growing conditions) |
| Open-Pollinated Pervenets Selection, Northern (See Table 2) | 0.15 |
| Sunflower, high-oleic (Present Invention)[2] | |
| Plant | |
| No. 1 | 0.04 |
| No. 2 | 0.05 |
| No. 3 | 0.02 |
| No. 4 | 0.03 |
| No. 5 | 0.03 |
| No. 6* | 0.05 |
| No. 7 | 0.01 |
| No. 8 | 0.09 |
| No. 9 | 0.07 |

[1]Derived from data of Soldatov, "Chemical Mutagenesis in Sunflower Breeding," in PROC. 7th INT'L SUNFLOWER CONFERENCE (Krasnodar, USSR 1976) 352-57; Kharchenko, "Genotypic and Phnotypic Mechanisms Ensuring Regulation of Fatty Acid Biosynthesis in Sunflower Seeds," Fiziologiya-Rastenii (Russ.) 26:1226-32 (1979).
[2]Oleic acid - and linoleic acid-content values for oil from seed of plants Nos. 6-9 were determined by gas chromatographic analysis. See Zimmer & Zimmerman, Crop Sci. 12:859 (1972). For oil from seed of plants Nos. 1-5, fatty acid profiles were ascertained using the protocol described for samples M and T in Table 2.
*From line designated SIGCO 416R.

White seed color, which is known to occur, for example, in certain open-pollinated Argentinean varieties, results from a lack of pigment in all three seed coat layers, and is a dominant trait relative to black color. Stripping of the seed, on the other hand, is caused by uneven pigmentation in the outer seed coat layer and is dominant over sold color pigmentation. When color is absent in the innermost layer, seeds are black (or brown) and white striped. When the black coloration of the inner layer is present the stripes may range in color from near white to various shades of gray.

In accordance with the present invention, a high-oleic sunflower seed possessing a white seed coat is obtained by crossing a line or variety comprising Pervenets germplasm which encodes high oleic acid content with a parent possessing the genetic determinant for white seed color. One or both of the parents in the aforementioned cross may be pure-breeding for the high oleic trait. An example of a suitable, commonly available, source for the white-color determinant is the Argentinean variety "Impira INTA." A white-seeded selection from Impira INTA, designated SIGCO 4117B, was crossed, pursuant to the present invention, with the Pervenets-derived line SIGCO 41B. (The latter line is the pollen-producing counterpart to the above-described CMS line, SIGCO 41A.) The resulting hybrid was self-pollinated over several generations to produce lines that yielded sunflower seeds, exemplary of a preferred embodiment of the present invention, which combined white seed color with an oleic acid content of approximately 80% or greater.

A white seed-bearing sunflower line, as described above, is preferably converted to cytoplasmic male sterility, in accordance with the present invention, and used as a female parent for producing high oleic hybrids which combine white coated seeds and high oleic acid content with other desirable traits, such as resistance to diseases and insects, high oil percentage, and improved agronomic traits.

Male parents for producing a white seeded hybrid with a white seed-bearing, high-oleic CMS parent of the present invention can be obtained by crossing a sunflower line or variety which carries the white-color determinant with a Pervenets-derived line that incorporates the genetic determinant for fertility restoration. The resultant hybrid can be self-pollinated over several generations to produce a line which expresses white seed color and high oleic acid content, preferably in combination with commercially desirable agronomic characteristics and which is substantially homozygous for the fertility restorer determinant. The aforementioned, white seed-yielding line can then be used, following the present invention, as a male parent to cross with a female parent from a Pervenets-derived CMS line with white seed to produce a white seeded hybrid.

In another preferred embodiment of the present invention, the aforementioned high-oleic trait is expressed in a sunflower seed having some black coloration, but only in the armor layer of its seed coat, so that the overall seed coat color is gray. Starting material for a gray-coated, high-oleic sunflower seed within the present invention is preferably produced by the procedures described in the preceding paragraphs for developing white seed-bearing, high oleic male and female parents. The white seeded lines can then be used to produce a gray-seeded hybrid by crossing a white seed-bearing, high oleic CMS parent with a black-seeded high oleic male parent, such as SIGCO 853R, or by crossing a black-seeded oleic CMS parent, such as SIGCO 41A, with a white seed-bearing, high oleic male parent. The high-oleic seed obtained from such a cross is gray colored, and thus is readily distinguishable from conventional, black-coated sunflower seed types.

In a manner similar to that described for developing white and gray-seeded, high oleic acid sunflowers, lines and hybrids with black (or brown) and white striped seed can be produced, in accordance with the present invention, which possess an oleic acid content of 80% or greater. In this embodiment, crosses are made using lines or varieties that have white striped seeds, such as commonly occur among nonoilseed or confection-type sunflowers. The production process is otherwse similar to that describe above for the white-seeded embodiment of the present invention.

To further illustrate the preferred embodiment described in the preceding paragraph, a high-oleic selection from the cross between the USDA restorer, RHA274, and the Pervenets cultivar was hybridized with a white-seeded restorer line, designated SIGCO 273W. After several generations of self-pollinating the resultant hybrid, a line was produced, designated SIGCO 416R, which yielded white seed having a high oleic acid content and a low linoleic acid content (see, e.g., plant No. 6 in Table 3). Seed from the line was used as a male parent for crossing with the black-seeded Pervenets female parent from SIGCO 41A line. The seed produced by the $F_1$ progeny was gray in color and possessed on oleic acid content in excess of 80%.

Small amounts of seed (100 seeds or less) of the SIGCO 41A, SIGCO 41B, SIGCO 853R, SIGCO 4117B, SIGCO 273W and SIGCO 416R are available from the Lubrizol Corporation, 29400 Lakeland Boulevard, Wickliffe, Ohio (USA) 44092.

What is claimed is:

1. A sunflower oil containing, relative to the total fatty acid content of said oil, approximately 80% or greater of oleic acid, said oil having a ratio of linoleic acid content to oleic acid content of less than about 0.09.

2. A sunflower oil according to claim 1, wherein said ratio is between about 0.01 and about 0.09.

3. A sunflower oil according to claim 1, wherein said oleic acid content is between about 80% and about 94%.

4. A sunflower oil according to claim 2, wherein said oleic acid content is about 87-88%. oleic acid 5. A sunflower oil according to claim 2, wherein said oleic acid content is about 92%.

6. A sunflower oil according to claim 2, wherein said oleic acid content is about 94%.

7. A sunflower oil produced by a process comprising the step of extracting oil from a substantially homogeneous assemblage of sunflower seeds, said sunflower oil having an AOM value between about 60 and about 100 hours.

8. A sunflower oil according to claim 7, wherein said assemblage of seeds has a ratio of the amount of linoleic acid in said seeds to the amount of oleic acid in said seeds of less than about 0.09.

9. A sunflower oil according to claim 8, wherein said ratio is between about 0.01 and about 0.09.

10. A sunflower oil according to claim 7, wherein said oil has an oleic acid content of about 80% or greater, relative to the total fatty acid content of said oil.

11. A sunflower oil according to claim 10, wherein said oil has an oleic acid content of about 87-88%.

12. A sunflower oil according to claim 10, wherein said oil has an oleic acid content of bout 92%.

13. A sunflower oil according to claim 10, wherein said oil has an oleic acid content of about 94%.

* * * * *

REEXAMINATION CERTIFICATE (3168th)

United States Patent [19]

Fick

[11] B1 4,743,402

[45] Certificate Issued Apr. 8, 1997

[54] NOVEL SUNFLOWER PRODUCTS AND METHODS FOR THEIR PRODUCTION

[75] Inventor: Gerhardt N. Fick, Breckenridge, Minn.

[73] Assignee: SIGCO Research Inc., Breckenridge, Minn.

Reexamination Requests:
No. 90/001,886, Nov. 9, 1989
No. 90/002,516, Nov. 22, 1991

Reexamination Certificate for:
Patent No.: 4,743,402
Issued: May 10, 1988
Appl. No.: 769,502
Filed: Aug. 26, 1985

Related U.S. Application Data

[62] Division of Ser. No. 672,359, Nov. 16, 1984, Pat. No. 4,627,192.

[51] Int. Cl.$^6$ ........................................... C11B 1/10
[52] U.S. Cl. ............................ 554/223; 426/601; 554/9
[58] Field of Search ...................... 260/412.2; 426/601; 554/9, 127, 223

[56] References Cited

U.S. PATENT DOCUMENTS 3,842,538  10/1974  Barabas ........................................ 47/58
4,378,655  4/1983   Johnson ........................................ 47/58

OTHER PUBLICATIONS

Soldatov et al., *Proceedings of the 7th International Sunflower Conference*, pp. 352–357 (1976), "Chemical Mutagenesis in Sunflower Breeding".

Pukhalsky et al., *Proceedings of the 8th International Sunflower Conference* Jul. 23–27, (1978), "Achievements of Sunflower Breeding in the USSR".

Fick, JAOCS 60: (7) 1252–1253 (1983), "Genetics and Breeding of Sunflower".

Poehlman, Breeding Field Crops, Holt Rinehart—Winston, NY, 1959 pp. 33–34.

Knowles reprinted from JAOCS 46: 130–132 (1967) "Modifications of Quantity and Quality of Safflower Oil Through Plant Breeding".

Knowles, *Economic Botany* 37: 423–433 (1983) "Genetics and Breeding of Oilseed Crops".

Vick and Miller et al., in *Proceedings Sunflowers Researchers Workshop* 9: 8–9, Feb. 1, 1984, "Releases of ND–01, A High Oleic Acid Sunflower Synthetic".

Beard et al., Current Research Information System (CRIS) Investigators Reports for the U.S. Department of Agriculture, Genetics and Breeding Research, Univ. of California Farm (Jan. 27, 1983).

Urie, Current Research Information System (CRIS) Investigators Report for the U.S. Dept. of Agriculture, Genetics and Breeding Research, Univ. of California Farm (Oct. 3, 1983).

Urie, *Proceedings Sunflower Researchers Workshop* 9: 9–10 (Feb. 1, 1984), "Inheritance of Very High Oleic Acid Content in Sunflower".

Urie, 25 Crop Science pp. 986–989 (1985), "Inheritance of High Oleic Acid in Sunflower".

Fick, Sunflower Science and Technology (J.F. Carter (ed.)), pp. 279–338 (1978) "Breeding and Genetics".

Fick, JAOCS 59 (4): 281a (Apr. 1982) "Genetics and Breeding of Sunflower".

Miller et al., *Proceedings, Sunflowers Research Workshop* p. 10, Jan. 26, 1983 "Inheritance of High Oleic Fatty Acid Content in Sunflower".

(List continued on next page.)

*Primary Examiner*—David T. Fox

[57] ABSTRACT

A sunflower seed is disclosed which has both a high oleic acid content and a low linoleic acid content. Also disclosed is a sunflower seed which has a white or gray seed coat and which contains approximately 80% or greater by weight of oleic acid. Also described are novel sunflowers for producing the disclosed seed and an oil product derived from the seed.

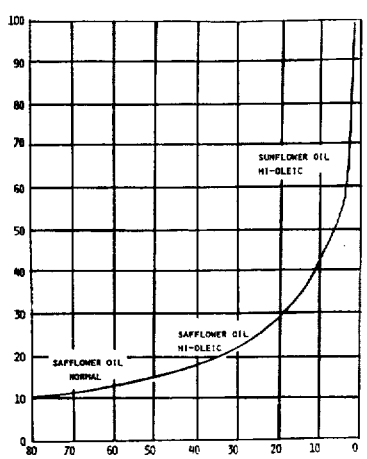

OTHER PUBLICATIONS

Beard et al., Current Research Information System (CRIS) Investigators Report for the U.S. Department of Agriculture, Research Work Unit/Project Description—Progress Report, Work Unit/Project No. 5306-20080-006-00D dated Aug. 2, 1988 CRIS ID. No. 821400 (Sep. 14, 1976 to Sep. 30, 1983).

Auld et al. 1992. Crop Sci. 32(3):657–662.

Fernandez–Martinez et al. 1989. Euphytica 41:39–51.

Kharchenko et al. pp. 20–22 In: V.S. Puitovata All–Union Scientific Research Institute of Oil–Bearing Crops, Krasnodar, USSR.

Agrios, G. p. 779 In: Plant pathology, 3rd edition, Academic Press, Inc.: New York.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–13 is confirmed.

New claims 14–21 are added and determined to be patentable.

*14. A sunflower oil containing, relative to the total fatty acid content of said oil, approximately 80% or greater oleic acid, said oil having a ratio of linoleic acid content to oleic acid content of less than about 0.09, and said oil being extracted from a substantially homogeneous assemblage of sunflower seeds which are obtained from plants that are the products of crosses between (A) plants from one or more sunflower lines which are true breeding for said oleic acid content and (B) plants from a second group of one or more sunflower lines.*

*15. A sunflower oil according to claim 14, wherein said ratio is between about 0.01 and about 0.09.*

*16. A sunflower oil according to claim 14, wherein said oleic acid content is between about 80% and about 94%.*

*17. A sunflower oil according to claim 15, wherein said oleic acid content is about 87–88% oleic acid.*

*18. A sunflower oil according to claim 15, wherein said oleic acid content is about 92%.*

*19. A sunflower oil according to claim 15, wherein said oleic acid content is about 94%.*

*20. A sunflower oil containing, relative to the total fatty acid content of said oil, approximately 80% or greater oleic acid, said oil having a ratio of linoleic acid content to oleic acid content of less than about 0.09 and an AOM value between about 60 and about 100 hours, and said oil being extracted from a substantially homogeneous assemblage of sunflower seeds which are obtained from plants that are the products of crosses between (A) plants from one or more sunflower lines which are true breeding for said oleic acid content and (B) plants from a second group of one or more sunflower lines.*

*21. A sunflower oil produced by a process comprising the step of extracting oil from a substantially homogeneous assemblage of sunflower seeds, said sunflower oil having (i) an AOM value between about 60 and about 100 hours, (ii) a ratio of linoleic acid content to oleic acid content of less than about 0.09, and (iii) an oleic acid content of about 80% or greater, relative to the total fatty acid content of said sunflower oil.*

\* \* \* \* \*